United States Patent [19]

Parnell

[11] Patent Number: 5,015,474
[45] Date of Patent: May 14, 1991

[54] COMPOSITION FOR IMPARTING MOISTURE TO A SUBSTRATE

[75] Inventor: Francis W. Parnell, Ross, Calif.

[73] Assignee: Parnell Pharmaceuticals, Inc., San Rafael, Calif.

[21] Appl. No.: 499,952

[22] Filed: Mar. 26, 1990

Related U.S. Application Data

[63] Continuation-in-part of Ser. No. 275,124, Nov. 22, 1988, Pat. No. 4,938,963.

[51] Int. Cl.⁵ .............................................. A61K 35/78
[52] U.S. Cl. .................................. 424/195.1; 424/64; 424/427; 424/430; 424/433; 424/434; 424/436; 424/440; 424/DIG. 15
[58] Field of Search .................. 424/440, 195.1, 64, 424/DIG. 15, 430, 433, 427, 434, 436

[56] References Cited

U.S. PATENT DOCUMENTS

| | | | |
|---|---|---|---|
| 3,965,908 | 6/1976 | Posthuma et al. | 128/303 R |
| 4,029,815 | 6/1977 | Sherlock et al. | 514/615 X |
| 4,128,631 | 12/1978 | Lundmark et al. | 424/70 |
| 4,151,270 | 4/1979 | Ream et al. | 424/48 |
| 4,184,974 | 1/1980 | Van Leuven | 252/106 |
| 4,209,505 | 6/1980 | Mikhail | 424/54 |
| 4,232,003 | 11/1980 | Posthuma et al. | 424/487 |
| 4,347,237 | 8/1982 | Evenstad et al. | 424/433 |
| 4,438,100 | 3/1984 | Balslev et al. | 424/104 |

OTHER PUBLICATIONS

Coon, *The Dictionary of Useful Plants*, pp. 20 & 152, (1974).
Coon, *Using Plants for Healing*, p. 122, (1963).
Fox et al., *J. Am. Dental Assoc.*, vol. 110, pp. 519–525, (1985).
Grieve, *A Modern Herbal*, vol. II, p. 865, (1959).

*Primary Examiner*—Jose G. Dees
*Assistant Examiner*—Vera C. Clarke
*Attorney, Agent, or Firm*—Irell & Manella

[57] ABSTRACT

Methods and compositions are provided for alleviating the dryness of a dermal or mucosal membrane substrate. The compositions are formulated from eriodictyon fluid which is a Yerba Santa extract and viscous excipients, and may be in the form of an aqueous vaginal douche, a cream or a suppository. The compositions may additionally contain a lubricant compound effective to provide lubrication and relieve frictional irritation on the affected area. Preservatives, topical anesthetics, coloring agents, emulsifiers, and the like may be included in the compositions as well. The Yerba Santa-based compositions of the invention are topically administered to an affected patient to alleviate the symptoms of dryness.

34 Claims, No Drawings

COMPOSITION FOR IMPARTING MOISTURE TO A SUBSTRATE

This is a continuation-in-part of pending U.S. application Ser. No. 07/275,124, filed Nov. 22, 1988, now U.S. Pat. No. 4,938,963, to which application is claimed priority under 35 U.S.C. §120 and which application is incorporated herein by reference.

FIELD OF THE INVENTION

The invention relates generally to topical compositions. More particularly, the invention relates to novel topical compositions for alleviating the dryness of a substrate such as the skin or mucosal membranes of an affected patient. The active ingredient of the novel composition is Yerba Santa fluid extract, which is eriodictyon fluid.

The invention also encompasses methods of treating dryness comprising administering an eriodictyon fluid-based composition to a substrate in order to relieve or prevent dryness.

BACKGROUND OF THE INVENTION

All mammals, and in particular humans, can suffer from dryness on particular areas of the body. The skin and mucosal membranes of the body are most often affected. Dryness of the skin or mucosal membranes can be cosmetically unattractive. In addition, the dryness can result in a certain degree of itching and pain. With respect to mucosal membranes, the dryness is the result of the generation of an insufficient quantity of mucoproteins and mucopolysaccharides on the affected area to hold fluid in contact with the cells. When insufficient moisture is present, the mucoproteins and mucopolysaccharides cannot create a sufficient barrier to irritation and infection. Accordingly, the affected individual is subjected to a higher degree of local infections with respect to the affected area, and such local infections can spread systemically. When such a systemic infection results, the consequences can be quite serious. Accordingly, it is important not only to relieve dryness in affected areas, but also to prevent the initial formation of dryness and therefore prevent the initial infections.

In our earlier application titled "Method and Composition for Treating Xerostomia", we discussed compositions and methods of treating that particular type of dryness. Xerostomia is a condition in which the salivary glands do not produce sufficient quantities of saliva. This causes discomfort which can in some cases be quite severe. Without saliva, the mouth burns and the throat and tongue can undergo radical changes. Teeth can decay rapidly and the tongue can become smooth, cracked and vulnerable to infection. There is often a loss of taste and, because saliva contains important digestive enzymes, there are often problems with digestion.

Cases of xerostomia may vary from the mild, in which only slight dryness is experienced, to severe cases in which the patient will have serious problems with mastication, swallowing, digestion, speech, and the like. As noted in U.S. Pat. No. 4,438,100 to Balslev et al., there are a number of causes of xerostomia, including the physiological (e.g., age, menopause, postoperative conditions, dehydration), as well as the psychic (nervousness). The reasons for mouth dryness may also be pharmacological (e.g., as a common side effect of many medications, including diuretics, antiarthritics and antidepressants) or as a result of radiotherapy. In addition to causing dry mouth, these factors can cause dryness of other areas such as vaginal dryness. The most severe cases of xerostomia, as well as other types of dryness are caused by radiation therapy (after head and neck surgery) and by autoimmune diseases such as lupus, Sjogrens Syndrome, and rheumatoid arthritis. See, for example, P. C. Fox et al., *J. Am. Dental Assoc.* 110:519-525 (1985).

A number of different compositions and methods for treating various types of dryness are described within the literature. For example, U.S. Pat. No. 4,232,003 issued Nov. 4, 1980 to Posthuma et al. discloses a composition referred to as a synthetic physiological mucous which is indicating as having particular usefulness in connection in treating the dryness of vaginal tissues and as a surgical lubricant. The composition is a pituitous aqueous solution of a high molecular polyacrylamide. Such synthetic mucous compositions and methods for using such compositions to treat dryness are also disclosed within U.S. Pat. No. 3,965,906 issued June 29, 1976.

The general concept of imparting lubricicity to a substrate such as skin, hair or mucous membranes is discussed within U.S. Pat. No. 4,128,631 issued Dec. 5, 1978. The inventors disclosed the use of a composition which includes a high molecular weight salt having a particular structural formula and molecular weight range.

A more specific type of lubricating composition in the form of a vaginal suppository is disclosed within U.S. Pat. No. 4,347,237 issued Aug. 31, 1982. The suppository is solid at room temperature and melts at body temperature due to its composition which includes a variety of different types of water soluble polyoxy alkylene polyol components.

As indicated above, the literature includes a number of disclosures of compositions and methods of applying those compositions to a substrate such as skin or mucous membranes in order to improve lubrication or relieve dryness. The effect is generally obtained by the application of a synthetic lubricant or a synthetic moisturizer and not by the inclusion of an active ingredient within the composition. However, U.S. Pat. No. 4,184,974 issued Jan. 22, 1980 to Leuven discloses a lubricant composition which includes a topical biocidal agent. A similar type of composition containing such a biocidal agent is disclosed within U.S. Pat. No. 4,267,168 issued May 12, 1981.

The present invention is premised on the surprising discovery that the oil extracted from the Yerba Santa plant (*Eriodictyon californicum; Eriodictyon qlutinosum;* also known as "consumptive's weed"; "bear's weed" "mountain balm" and "gum plant") is extremely effective in providing long-lasting relief of a variety of types of mild to severe dryness of dermal and mucosal membranes, with no unpleasant side effects.

The Yerba Santa plant is an evergreen shrub indigenous to the hills and mountains of California and northern Mexico, and was long used by Indians for a number of purposes. See, e.g., A. R. Hutchens, *Indian Herbalogy of North America,* Ontario: Merco, 1975, at pp. 317–318. A number of references to the Yerba Santa plant teach its use as an expectorant (e.g., N. Coon, *The Dictionary of Useful Plants,* Emmaus, Pa.: Rodale Press, (1974)), in treating colds, sore throats, catarrh, stomach aches, vomiting and diarrhea (see A. R. Hutchens, *supra*), in treating hemorrhoids (D. G. Spoerke, *Herbal Medica-* tions, Santa Barbara, Cal.: Woodbridge Press, 1980, at p. 183), in treating diseases of the lung (*Los Remedios de la Gente: A Compilation of Traditional New Mexican Herbal Medicines and Their Use*, compiled by M. Moore, 1977), and in masking the taste of quinine and other bitter medications (Spoerke, supra; see also G. E. Trease et al., *Pharmacognosy*, London: Cassell & Colber, 1978, at p. 463)).

Publications discussing the Yerba Santa plant include the Coon, Hutchens, Moore, Spoerke, and Trease et al. references, cited in the preceding section, as well as V. J. Vogel, *American Indian Medicine*, The University of Oklahoma Press, 1970, at pp. 83, 399–400; W. H. Lewis et al., *Medical Botany: Plants Affecting Man's Health*, New York: John Wiley & Sons, 1977, at p. 301; P. Huson, *Mastering Herbalism: A Practical Guide*, New York: Stein and Day, 1974, at p. 32; B. C. Harris, *The Compleat Herbal*, Barre, Mass.: Barre Publishers, 1972, at p. 197; N. Coon, *Using Plants for Healing*, Hearthside Press, 1963, at p. 122; M. Grieve, *A Modern Herbal*, vol. 22, New York: Hafner Publishing Co., 1959, at p. 865; and V. E. Tyler et al., *Pharmacognosy*, Philadelphia: Lee & Febiger, 1981, at p. 148.

SUMMARY OF THE INVENTION

The invention includes a method for alleviating dryness comprising administering a composition of eriodictyon fluid extract topically to a patient. The composition may also be administered in pure form, but is preferably administered in a form combined with other viscous excipient materials.

It is an object of the invention to provide a method for treating various types of dermal and mucosal membrane dryness, comprising topically administering, to an affected individual, a composition containing an effective amount of eriodictyon fluid to alleviate the symptoms of dryness, the composition comprising the eriodictyon fluid in and a viscous excipient.

It is another object of the invention to provide such a composition to be topically administered, which composition contains eriodictyon fluid and a suitable excipient material which is pharmacologically compatible with the eriodictyon fluid and nonirritating to the area to which it is applied.

It is yet another object of the invention to provide such a method wherein the composition to be administered, in addition to containing Yerba Santa extract in the form of eriodictyon fluid includes a bactericidal compound in an amount effective to kill bacteria on the area of application.

It is a further object of the invention to provide such a method wherein the composition to be administered contains eriodictyon fluid, a topical anesthetic, and a preservative.

It is still a further object of the invention to provide a Yerba Santa-based composition for treating various types of dryness, useful in the aforementioned method.

It is yet a further object of the invention to provide a composition for treating dryness which contains eriodictyon fluid and one or more excipients and additional active components selected from the group consisting of a preservative, a bactericide, an antiviral, and an anesthetic.

These and other object, advantages and features of the present method and compositions for alleviating dryness will become apparent to those persons skilled in the art upon reading the details of the composition and usage as more fully set forth below, reference being made to the accompanying general and specific composition examples forming a part hereof.

DETAILED DESCRIPTION OF THE PREFERRED EMBODIMENTS OF THE INVENTION

Before the present eriodictyon fluid based composition and method for treating and preventing dryness are described, it is to be understood that this invention is not limited to the particular compositions or methods described as such compositions and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a lubricant" includes mixtures of lubricants, reference to "an excipient" includes reference to mixtures of such excipients, reference to "the method" or "the step" includes a variety of such methods or steps of the type known to those skilled in the art, and so forth.

In its broadest sense, the invention encompasses a method of treating skin and/or mucosal dryness by administration of a topical composition of Yerba Santa fluid extract to an affected patient. By "Yerba Santa fluid extract" as used herein is meant the eriodictyon fluid which may be extracted from dried Yerba Santa leaves. One exemplary method for obtaining this Yerba Santa fluid extract is set forth in *Remington's Pharmaceutical Sciences*, 17th Ed., 1985, at pp. 1286 and 1516, which is incorporated herein by reference to disclose such an extraction method. As described in detail therein, the dried Yerba Santa plant is preferably processed in alcohol and water, followed by straining, pressing and clarification by, e.g., decantation or filtration.

In a preferred embodiment, the composition is administered as a topical composition of eriodictyon fluid extract in one or more excipients. The composition will preferably contain in the range of 0.25 wt.% to 10 wt.%, more preferably 0.5 wt.% to 5.0 wt.%, and most preferably about 1.25 wt.% eriodictyon fluid extract. Depending on the area to which the composition is applied the composition will also contain one or more additional active ingredients such as bactericides, antivirals, and anesthetics, in total comprising about 1.0 wt.% to 30 wt.%, more preferably 10 wt.% to 20 wt.%, with the amount varying with the class and specific type of ingredient used.

It is preferred that the composition also contain a preservative which will increase the shelf life of the composition. Preferred compounds include quarternary ammonium bacteriostates such as benzalkonium chloride, present in an amount ranging from about 0.25 wt.% to about 5.0 wt.%, preferably about 0.5 wt.%. Incorporation of any of phenyl mercuric acetate, thimerosal, or benzyl alcohol into the present composition also serves to retard bacterial growth in the composition.

Specific examples of formulation ingredients other than those already referred to and preferred formulation amounts will be exemplified hereinbelow.

As a dissolution-assisting agent, there may be mentioned, for example, non-ionic surface active agents, such as polyoxyethylenesorbitan monooleate, polyoxyethyleneoxystearic acid triglyceride, polyethylene glycol, etc.

A thickening agent includes, for example, polyvinylpyrrolidone, methylcellulose, hydroxypropylmethylcellulose, hydroxyethylcellulose, hydroxypropylcellulose, etc.

As an antiseptic, those conventionally used may be mentioned, for example, benzalconium chloride, cetylpyridinium chloride, chlorobutanol, methylparaben, propylparaben, etc.

A chelating agent, such as sodium ethylenediaminetetraacetate (EDTA-Na), may be used.

The pH of the solution of this invention is preferred to be 6.5-8.5, particularly about 7.5

A particularly preferred embodiment of the invention is a liquid composition in a form suitable for use as a vaginal douche. In such a composition the eriodictyon fluid is present in an aqueous carrier (largely pure water) with a small amount of acetic acid to adjust the pH to that which is equal to the vagina (about 5.0). Such a liquid composition is generally comprised of about 90-99% water and about 1-10% of the eriodictyon fluid of the invention. After providing for the essential components of the water and eriodictyon fluid, the pH of the composition is adjusted by adding acetic acid in an amount which will decrease the pH of the final solution to somewhere in the range of 4.0 to 6.0, and more preferably about 5.0. The composition preferably includes a preservative such as sodium benzoate, which is generally present in relatively small amounts such as in the range of 0.1 wt.% to about 1 wt.%, more preferably about 0.25 wt.%.

Another particularly preferred embodiment of the present invention is a liquid composition in the form of a nasal decongestant spray. Such a composition is largely comprised of water. It may include 90-99% water and 1-10% of eriodictyon fluid. Such a nasal spray composition preferably includes a component which aids in nasal decongestion, such as ephedrin sulfate in an amount of 0.05 to 1 wt.%, and more preferably about 0.25 wt.%. In order to provide for additional lubrication, it is often preferable to include glycerine in an amount of 1-5 wt.%, more preferably about 3 wt.%. In that the composition is to be used for nasal administration, the saline content of the solution is adjusted so that its saline content is approximately equal to that of the nasal environment to which it will be applied. Further, the pH of the composition is adjusted to a pH compatible with nasal membranes, which can be accomplished by buffers known to those skilled in the art.

In a particularly preferred embodiment of the nasal spray, the eriodictyon fluid is present in an amount of about 1.5%, ephedrin sulfate 0.25%, glycerine 3%, sodium chloride 0.80%, EDTA and benzalkonium chloride, buffered to nasal pH.

The liquid nasal composition of the invention provides a nasal mucosal decongestant and lubricant which is useful in treating allergic rhinitis, vasomotor rhinitis, rhinitis medicamentosa, rhinitis sicca, sinusitis, and atrophic rhinitis.

The liquid nasal composition of the invention is applied by spraying the composition into the nostrils once or twice while tilting the head back. The administration may be repeated two or three times a day or as directed in order to obtain the desired relief of dryness and/or decongestion of the nasal passages.

One important embodiment of the invention is a moisturizing lubricant in the form of a suppository, which lubricant is designed specifically for the human vagina. An aspect of this invention relates to a pre-coital lubricant in suppository form. Still another aspect of this invention relates to a method for lubricating the human vagina by insertion of a solid suppository which melts to form a lubricant at human body temperature.

When insertion of any material into a human body canal (particularly the vagina or anus) is desirable, suppositories have advantages and are often preferred by patients, doctors, and other users. The suppository art is a highly developed one, particularly with respect to suppositories which provide a matrix for releasing some medicament. Such suppositories can be made lubricious; see, for example, U.S. Pat. No. 3,776,001 (Hanke), issued Dec. 4, 1973. Medicators, tampons, and the like have also been made lubricious, at least on their surfaces.

Suppositories of this invention are solid at normal ambient temperatures but melt at human body temperature to form a substantially homogeneous liquid having the appearance of a single liquid phase, even though a glyceride of an aliphatic carboxylic acid is distributed through this homogeneous liquid. In either the liquid or solid state, suppositories of this invention could include the following non-active components:

(a) a continuous phase comprising a polyoxyalkylene polyol component consisting essentially of polyethylene glycols having a molecular weight within the range of 400 to 5,000, so that this component will have a melting range low enough for the purposes of this invention;

(b) about 10-60 parts per 100 parts by weight of the aforementioned polyol component (and typically 10-30% by weight of the suppository), of a nonionic surfactant having an HLB value greater than 12 (typically this surfactant dissolves in the polyol component); and (c) about 10-40 parts per hundred, based on the weight of the polyol component, of a glyceride (preferably a triglyceride) of an aliphatic carboxylic acid, which glyceride is uniformly distributed throughout the continuous phase with the aid of the nonionic surfactant.

The human vagina can be pre-coitally lubricated with a suppository of this invention by inserting the solid suppository and permitting it to melt within the vaginal canal prior to coitus. The melting is generally complete within a very few minutes. If desired, the insertion can take place up to a few hours before coitus.

Suppositories of this invention are made by melting the polyethylene glycols at a moderately elevated temperature, thereby obtaining a homogeneous melt. The preferred nonionic surfactant (including surfactant combinations) can be dissolved in the melt. The resulting hot mixture is a suitable medium for distributing the glyceride, which is the primary lubricating substance. When a suitable blend has been formed, it can be cast into the form of suppositories using molds or a suppository packaging material that serves as both mold and package.

Regarding suppositories the components, the relative amounts of those components and methods of making such are described in detail in U.S. Pat. No. 4,347,237 which is incorporated herein by reference to disclose such. It is also pointed out that other U.S. patents are cited in U.S. Pat. No. 4,347,237 to describe the suppository art in general. A variety of different excipients could be used in combination with the eriodictyon fluid of the invention to form a useful suppository of this invention.

The eriodictyon fluid component promotes the release of natural moisture from any substrate it is applied to such as dermal and mucous membrane substrates. However, the topical formulations of the invention which include suppositories are preferably formulated so that for example, even in the absence of natural vaginal moisture, a fully or partially melted suppository or vaginal insert of this invention has lubricating properties. The combination of ingredients of this invention preferably allows the melted lubricating substance to become miscible with the vaginal moisture present even in small amounts. As the insert or suppository melts and mixes with any vaginal moisture, it spreads readily throughout the vagina. In addition, the lubricity of the invention is not reduced due to evaporation of moisture during coitus.

The excipient materials for topical compositions of the invention may include glycol, glyceride, lubricant, and surfactant components further modified with a lower aliphatic monomeric hydrophilic polyol which will dissolve in the glycol phase. A preferred monomeric polyol is glycerin. Pigments, fillers, extenders, preservatives, and antioxidants can also be included in the composition, but it is ordinarily preferred to avoid the use of any filler, extender, or pigment which will leave a visible solid residue. For antioxidant or preservative effects, various FDA-approved compounds are suitable, including the conventional alkylated hydroxy aromatic compounds such as BHT (butylated hydroxytoluene) or BHA (butylated hydroxyanisole).

Topical and suppository compositions of the invention can be formulated by dispersing small amounts 1% to 15% by weight of eriodictyon fluid in one or more (preferably a blend) of polyoxyethylene or polyethylene glycols. These glycols contain an oxyethylene chain with an extraordinary compatibility with water and with a hydroscopicity of at least 0.1%, preferably at least 1% of glycerin. Because these polyethylene glycols make up such a large proportion of the lubricating suppository, it is preferred that a single such glycol (if used alone) or any combination of such glycols be solid at normal ambient temperatures (20°-25° C.) and preferably at moderately elevated temperatures which may inadvertently be reached during storage, e.g., 30° or 35° C. On the other hand, it is desirable that the glycol component be capable of melting at temperatures close to human body temperature (e.g., 37° C.). The melting point of the glycol component can of course be depressed by blending into it compatible liquids or low-melting solids. Nevertheless, it is preferable that, in the absence of such liquids or low-melting solids, the glycol component have a melting point or melting range low enough to insure the formation of a clear molten liquid at less than about 75° C., more preferably at less than about 55° or 60° C. Among the low-melting solids and liquids which can provide the aforementioned melting point depressant effect are low molecular weight polyoxyethylene glycols which are available in molecular weights well below 1,000 (equivalent weights well below 500). It is preferred however to keep the molecular weight of the lowest-melting glycol above about 400. A polyethylene glycol having an average molecular weight of about 500 could be a solid at 20° C., but may have the consistency of low-melting petrolatum. The particular glycol including its amount and molecular weight can be determined by those skilled in the art depending on the end results desired.

The pH of the product is preferably adjusted to that normally encountered in the mucus secretions for which the product is being substituted. The excipients should be stable in the useful pH range of about 3-10. For vaginal mucus substitution, the pH is adjusted to about 5-8, normally about 5, with a suitable acidic reagent or the like that has no significant epidermal or mucosal toxicity, such as citric acid or similar weak organic acids. Natural vaginal mucus has a normal pH of about 5, but this pH does vary a great deal such that the pH range of about 5-8 for the synthetic mucus is acceptable.

Compositions of the invention which are to be applied to a dermal substrate often contain emollients such as stearic acid, glycerol monostearate, mineral oil, glycerine, sesame oil, bees wax, lauryl, myristyl, cetyl or stearyl alcohols, lanolin, lecithin, sterols, isopropylmyristate, and as well any other recognized emollients. Emollients are typically used in the present invention at levels of from about 1% to about 50% by weight.

Astringents and antiseptics may be incorporated into the compositions of the present invention. A preferred astringent material is zinc phenolsulfonate. The foregoing material exhibits not only astringent but also antiseptic qualities and is of particular use in preshave formulations to make the beard "stand up". Humectants such as propylene glycol are also desirable ingredients for inclusion in personal care products to prevent drying of the skin. Allantoin is included in such compositions for its purported soothing and healing effects upon injured skin.

A variety of different biocidal agents can be included in the compositions of the invention. They may be added to kill bacteria or virus or both on the substrate. The inclusion of silver ions are known to have such an effect and can be included in amounts of 10 to 500 ppm by adding silver nitrate to the composition, Such biocidals are described in U.S. Pat. No. 4,267,168 issued May 12, 1981.

It is preferred that the composition contain one or more preservatives, typically an antioxidant present in an amount effective to retard oxidation and/or inactivation of the fluid extract. As with other additives, both active and inactive, the selection will be readily made by one skilled in the art. Examples of suitable preservatives include ascorbyl palmitate, butylated hydroxyanisole, butylated hydroxytoluene, potassium or sodium sorbate, sodium bisulfite, sodium metabisulfite, sorbic acid, sulfur dioxide, and sodium or potassium benzoate. A particularly preferred preservative for use herein is sodium benzoate.

Other components which may, if desired, be incorporated into the present composition include coloring agents, which may be either natural or synthetic, diluting agents, emulsifying agents, excipients, pH buffering agents, and the like.

The final pH of the composition of the invention can be adjusted over a wide range, e.g., 3-10. However, the lower pH 3 and upper pH 10 ends of the range are not generally desired. The pH of a particular composition is adjusted to match as closely as possible the pH of the biological environment the composition is to be applied to. Lower pHs of about 5 are generally preferred for vaginal use, whereas more neutral pHs around 7.0 to about 7.5 are useful for other uses such as ophthalmic compositions.

Suitable colorants include dyes that are generally suitable for food, drug and cosmetic applications, i.e., those known as "F. D. & C." dyes. Where the Yerba Santa composition is in aqueous form, acceptable dyes should be water soluble. Illustrative examples include the disodium salt of 5,5-indigotindisulfonic acid ("F. D. & C. Blue No. 2") and the monosodium salt of 4-[4-N-ethyl-p-sulfo-benzylamino)-diphenylmethylene]-[1-(N-ethyl-N-p-sulfonium-benzyl)-2,5 -cyclohexadienimine ("F. D. & C. Green No. 1"). Reference may be had to the Kirk-Othmer Encyclopedia of Chemical Technology, 3rd Ed., in Volume 6, for further F. D. & C. colorants and corresponding chemical structures.

The composition as just described is preferably administered as a viscous cream, which is readily prepared by admixing the Yerba Santa fluid extract with selected excipient components.

The composition may also be prepared as a suppository, with the preferred components and the preferred relative composition by weight being described below.

The excipient materials may include a number of substances of synthetic origin such as butadiene-styrene polymer, isobutyleneisoprene copolymer, paraffin, petroleum wax, polyethylene, polyisobutylene, polyvinylacetate, etc., plasticizers or softeners such as lanolin, stearic acid, sodium stearate, potassium stearate, glyceryl triacetate, glycerine, etc.

Waxes, including low melting point natural and synthetic waxes, petroleum waxes, paraffin waxes and microcrystalline waxes may also be incorporated into the suppository in order to obtain desirable texture and consistency.

Suppositories will typically be shaped solids containing the resinous Yerba Santa fluid extract in a base which slowly melts at body temperature. Preparation of suppository forms is well known in the art, and is described, for example, in *Remington's Pharmaceutical Sciences*, 17th edition, cited supra, at pages 1580–1584. Typically, the Yerba Santa extract is mixed with other optional compounds as described above. The resulting mixture is shaped and/or compressed into the desired form.

The amount of Yerba Santa extract administered will, of course, be dependent on the subject being treated, the severity of the dryness, and the judgment of the prescribing health care professional. However, an effective dosage regimen will typically be 1-2 tsp of a topical composition containing 0.25 wt.% to 10 wt.% Yerba Santa fluid extract, applied topically twice per day. It is preferred to measure so that the composition be retained in contact with the mucous membrane being treated for a time sufficient to allow the Yerba Santa fluid extract to fully coat and remain on the membrane for a substantial period of time. The coating should remain in place for sufficient time to allow the natural membrane to replace itself. Reapplication of the composition of the invention to the dry area may be and often is required in order to obtain the desired results.

EXAMPLES

The following examples are provided so as to provide those of ordinary skill in the art with a complete disclosure and description of how to make the compositions of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

Example 1

| Ingredients | Quantity |
| --- | --- |
| Excipient (carrier) | 90–99.0 wt. % |
| Yerba Santa Fluid Extract* | 1–10.0 wt. % |
| Other Components | 0–9.0 wt. % |

*Dried eriodictyon can be obtained from Meer Corporation, North Bergen, New Jersey; it can be used to prepare the fluid extract in a manner substantially as described in Remington's Pharmaceutical Sciences, 17th Ed., cited supra, on pages 1286 and 1516.

After preparation of the fluid extract, the above ingredients can be mixed to give a topical composition of Yerba Santa fluid extract.

Example 2

| Ingredients | Quantity |
| --- | --- |
| Excipient (lubricant cream) | 98.50 wt. % |
| Yerba Santa Fluid Extract* | 1.25 wt. % |
| Preservative | 0.25 wt. % |

One to two teaspoons of the above topical composition can be administered as needed to obtain relief from or prevent dryness.

Example 3

| Ingredients | Quantity |
| --- | --- |
| Excipient (aqueous) | 90.0–98.50 wt. % |
| Yerba Santa Fluid Extract* | 10.0–1.50 wt. % |

The aqueous excipient will preferably include pure water and acetic acid in sufficient amount to adjust the pH to about 5.0. The excipient also preferably includes a preservative such as sodium benzoate in an amount of about 0.1 to 0.5 wt.%. The solution can be used as a vaginal douche.

Example 4

| Ingredients | Quantity |
| --- | --- |
| Lubricant/Moisturizer | 98.50 wt. % |
| Yerba Santa Fluid Extract* | 1.25 wt. % |
| Sodium Benzoate | 0.25 wt. % |

This composition is in the form of a cream which can be applied to any dry area.

Example 5

| Ingredients | Quantity |
| --- | --- |
| Polyoxyalkylenepolyol | 98.75 wt. % |
| Yerba Santa Fluid Extract* | 1.00 wt. % |
| Sodium Benzoate | 0.25 wt. % |

This composition is a solid suppository at room temperature and melts at body temperature.

Example 6

| Ingredients | Quantity |
| --- | --- |
| Excipient | 96.75 wt. % |
| Yerba Santa Fluid Extract* | 1.00 wt. % |
| Sodium Benzoate | 0.25 wt. % |
| Biocidal Agent | 2.0 wt. % |

Example 7

| Ingredients | Quantity |
| --- | --- |
| Excipient (aqueous) | 95.75 wt. % |
| Yerba Santa Fluid Extract* | 3.00 wt. % |
| Sodium Benzoate | 0.25 wt. % |
| Acetic acid | 1.0 wt. % |

Example 8

| Ingredients | Quantity |
| --- | --- |
| Excipient (topical cream) | 97.50 wt. % |
| Yerba Santa Fluid Extract* | 1.25 wt. % |
| Sodium Benzoate | 0.25 wt. % |
| Antiviral Agent | 1.0 wt. % |

Example 9

| Ingredients | Quantity |
| --- | --- |
| Synthetic Mucous | 90.0–99.0 wt. % |
| Yerba Santa Fluid Extract* | 1.0–10.0 wt. % |
| Preservative | 0.25 wt. % |

Example 10

| Ingredients | Quantity |
| --- | --- |
| Polyoxyalkylenepolyal | 50.0 wt. % |
| Yerba Santa Fluid Extract* | 1.25 wt. % |
| Sodium Benzoate | 0.25 wt. % |
| Glycerine | 48.0 wt. % |
| Bacteriocidal Agent | 0.5 wt. % |

Example 11

| Ingredients | Quantity |
| --- | --- |
| Water | 90.0–99.0 wt. % |
| Eriodictyon Fluid | 1.0–10.0 wt. % |
| pH Buffer | 0.0–9.0 wt. % |

The above general example could, of course, include preservatives. The pH of the composition is adjusted to match the pH of the mucosal tissues to which the composition is applied.

Example 12

| Ingredients | Quantity |
| --- | --- |
| Water | 90.0–99.0 wt. % |
| Eriodictyon Fluid | 1.0–10.0 wt. % |
| pH Buffer | 0.0–9.0 wt. % |
| Sodium Chloride | 0.01–5.0 wt. % |

The above composition is most useful in connection with nasal sprays. The composition may further include other active components such as decongestants. The sodium chloride is added in an amount to adjust to the saline composition of normal nasal mucosal tissues, as is the pH of the composition.

While the present invention has been described with reference to the specific embodiments including methods and formulations for treating dryness, it should be understood by those skilled in the art that various changes may be made and equivalents may be substituted without departing from the true spirit and scope of the invention. In addition, many modifications may be made to adapt a particular substrate surface to be treated, excipient, material, composition of matter, process, process step or steps, to the objective, spirit and scope of the present invention. All such modifications are intended to be within the scope of the claims appended hereto.

I claim:

1. A method of imparting moisture to a substrate selected from the group consisting of skin and mucous membranes of an individual in need thereof, comprising the steps of:

contacting the substrate of said individual with erodictyon fluid in an amount sufficient to achieve an acceptable degree of moisture on the contacted tissue; and allowing the erodictyon fluid to remain in contact with and coat the substrate for sufficient time and in sufficient amount so as to cause the substrate of the individual to have moisture imparted thereto.

2. The method as claimed in claim 1, wherein the substrate is a mucous membrane.

3. The method as claimed in claim 2, wherein the mucous membrane is a vaginal tissue.

4. The method as claimed in claim 2, wherein the mucous membrane is a nasal tissue.

5. The method as claimed in claim 2, wherein the mucous membrane is a sinus tissue.

6. The method as claimed in claim 2, wherein the mucous membrane is a surrounding ocular tissue.

7. The method as claimed in claim 2, wherein the mucous membrane is an anal tissue.

8. The method as claimed in claim 2, wherein the mucous membrane is a lip tissue.

9. The method as claimed in claim 2, wherein the mucous membrane is a urethral tissue.

10. A topical composition, comprising:

a pharmaceutically effective amount of eriodictyon fluid; and a viscous excipient material pharmaceutically compatible with the eriodictyon fluid and nonirritating to a mucous membrane, the eriodictyon fluid being dispersed throughout the excipient material.

11. The topical composition as claimed in claim 10, further comprising:

a pharmaceutically acceptable preservative present in an amount effective to retard oxidation of the composition and retard bacterial growth therein.

12. The topical composition as claimed in claim 10, further comprising:

a bactericidal compound.

13. The topical composition as claimed in claim 10, further comprising:

an antiviral compound.

14. The topical composition as claimed in claim 10, further comprising:

a topical anesthetic.

15. The topical composition as claimed in claim 10, further comprising:
a pharmaceutically acceptable lubricant.

16. The topical composition as claimed in claim 10, further comprising:
a bactericidal compound and a topical anesthetic.

17. The topical composition as claimed in claim 10, wherein the viscous excipient material is comprised of propylene glycol.

18. The topical composition as claimed in claim 15, wherein the lubricant is glycerine.

19. The topical composition as claimed in claim 12, wherein the bactericidal compound comprises silver ions.

20. An aqueous vaginal douche composition, comprising:
a pharmaceutically effective amount of eriodictyon fluid; and
aqueous excipient material pharmaceutically compatible with the eriodictyon fluid and nonirritating to vaginal tissues, the eriodictyon fluid being dispersed throughout the excipient material.

21. The aqueous vaginal douche composition as claimed in claim 20, further comprising:
a pharmaceutically acceptable preservative present in an amount effective to retard oxidation of the composition and retard bacterial growth therein.

22. The aqueous vaginal douche composition as claimed in claim 20, wherein the aqueous excipient is comprised of water and acetic acid and the pH of the composition is in the range of about 4.0 to about 6.0.

23. The aqueous vaginal douche composition as claimed in claim 22, wherein the pH is about 5.0.

24. The aqueous vaginal douche composition as claimed in claim 20, further comprising:
a topical anesthetic.

25. The aqueous vaginal douche composition as claimed in claim 20, further comprising:
a pharmaceutically acceptable lubricant nonirritating to vaginal tissue.

26. An aqueous vaginal douche composition, comprising:
a pharmaceutically effective amount of eriodictyon fluid; and
aqueous excipient material pharmaceutically compatible with the eriodictyon fluid and nonirritating to a mucous membrane, the eriodictyon fluid being dispersed throughout the excipient material, the excipient comprising pure water and acetic acid in an amount sufficient to provide the composition with a pH of about 5.0.

27. The aqueous vaginal douche composition as claimed in claim 26, further comprising:
a pharmaceutically acceptable preservative present in an amount effective to retard oxidation of the composition and retard bacterial growth therein.

28. The aqueous vaginal douche composition as claimed in claim 26, further comprising:
a topical anesthetic, 29. The aqueous vaginal douche composition as claimed in claim 26, further comprising:
a pharmaceutically acceptable lubricant nonirritating to vaginal tissue.

30. The aqueous vaginal douche composition as claimed in claim 26 wherein the eriodictyon fluid is present in an amount in the range of about 1.0 wt.% to about 10.0 wt.%.

31. An aqueous nasal composition, comprising:
a pharmaceutically effective amount of eriodictyon fluid; and
aqueous excipient material pharmaceutically compatible with the eriodictyon fluid and nonirritating to nasal mucosal membranes, the eriodictyon fluid being dispersed throughout the excipient material, the excipient comprising pure water, sodium chloride, and a pH buffer, wherein the sodium chloride and pH buffer are present in sufficient amounts so as to provide for a composition with a saline content and pH compatible with nasal mucosal membranes.

32. The aqueous nasal composition as claimed in claim 31 further comprising:
a nasal decongestant.

33. The aqueous nasal composition as claimed in claim 31, wherein the eriodictyon fluid is present in an amount in the range of about 1.0 wt.% to about 10.0

34. The aqueous nasal composition as claimed in claim 31, further comprising:
glycerine in an amount of about 1.0 to about 5.0 wt.%.

* * * * *